United States Patent [19]

Young

[11] 4,283,573
[45] Aug. 11, 1981

[54] LONG-CHAIN ALKYLPHENOLS

[75] Inventor: Lewis B. Young, Skillman, N.J.

[73] Assignee: Mobil Oil Corporation, New York, N.Y.

[21] Appl. No.: 96,093

[22] Filed: Nov. 20, 1979

[51] Int. Cl.³ .............................................. C07C 37/11
[52] U.S. Cl. .................................... 568/794; 568/786; 568/789; 568/804
[58] Field of Search ............... 568/786, 789, 791, 794, 568/785, 804

[56] References Cited

U.S. PATENT DOCUMENTS

| | | | |
|---|---|---|---|
| 2,874,194 | 2/1959 | Dijkstra | 568/791 |
| 3,706,807 | 11/1972 | Etherington et al. | 568/791 |
| 3,728,408 | 4/1973 | Tobias | 568/791 |
| 3,872,173 | 3/1975 | Berthoux et al. | 568/786 |
| 3,876,710 | 4/1975 | Saito et al. | 568/786 |
| 3,992,455 | 11/1976 | Leston | 568/791 |

FOREIGN PATENT DOCUMENTS

| | | | |
|---|---|---|---|
| 1150209 | 4/1969 | United Kingdom | 568/791 |
| 185930 | 10/1966 | U.S.S.R. | 568/789 |
| 352869 | 7/1969 | U.S.S.R. | 568/791 |
| 539021 | 12/1976 | U.S.S.R. | 568/794 |

OTHER PUBLICATIONS

Venuto et al., "Journal of Catalysis" vol. 4, p. 81-98 (1966).
Webster's Seventh New Collegiate Dictionary, Merriam Co. Pub (1967) pp. 21 & 634, Springfield, Mass.
Webster's New World Dictionary of the American Language, World Pub Co. Cleveland & New York (1966) pp. 35 & 1098.
Wertheim "The Textbook of Organic Chemistry" (1947) Blakiston Co. Pub Philadelphia pp. 491, 493-494.

Primary Examiner—Werren B. Lone
Attorney, Agent, or Firm—Charles A. Huggett; Charles J. Speciale; Ronald J. Cier

[57] ABSTRACT

A method for producing long chain-length alkylphenols with preferential production of para-alkylphenols and placement of the phenolic moiety at the #2 position on the alkyl chain. The reaction is carried out in the presence of crystalline zeolites having a major pore dimension of about six to seven angstrom units.

15 Claims, 1 Drawing Figure

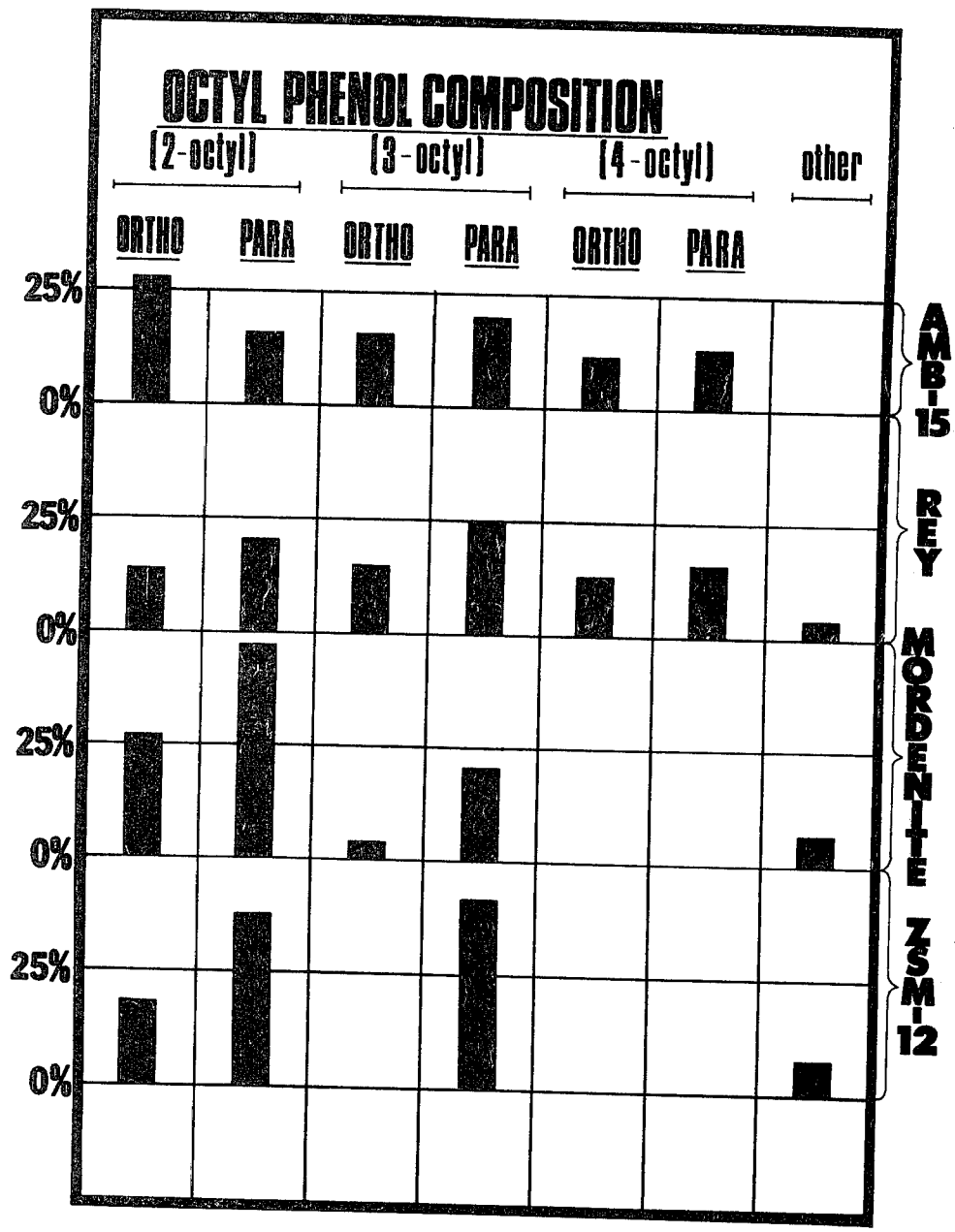

LONG-CHAIN ALKYLPHENOLS

BACKGROUND OF THE INVENTION

1. Field of the Invention

This invention relates to the preparation of alkyl-substituted phenols via reaction, in the presence of a catalytically active zeolite, of a phenol with an organic compound having an available alkyl group.

2. Description of the Prior Art

Several long-chain alkylphenols are known useful items of commerce. p-Nonylphenol, for instance, which is used primarily for surfactants, is currently produced in quantities of about 100 million pounds a year. Production of these compounds by conventional methods—for example, by the alkylation of phenol in the presence of conventional alkylation catalysts—is, however, somewhat problematic in that the reaction yields a broad spectrum of products. Isolation or enrichment of specific positional isomers is both difficult and expensive.

Traditionally, alkylation reactions are generally carried out at atmospheric pressure with the reactants in the liquid phase, utilizing catalysts such as sulfuric acid, boron trifluoride, aluminum chloride or strongly acidic ion exchange resins. Some zeolites, specifically REX and HY, have been reported in the scientific literature as catalyzing the reaction of 1-decyl alcohol with phenol at atmospheric pressure and 200° C. The product of that reaction was predominantly an ortho/para mixture of decylphenols with side chain attachment largely at carbons #2 and #3 of the alkyl group.

SUMMARY OF THE INVENTION

A method has now been discovered for producing alkyl-substituted phenolic compounds having a product spectrum unlike that obtained from conventional alkylation reactions. The method comprises contacting, in the presence of a specific type of shape selective crystalline zeolite catalyst, a phenolic compound with another organic compound which has an available, relatively long-chain, alkyl group to yield a product mixture rich in para-alkylphenols and also alkylphenols in which the aromatic ring is preferentially attached at the #2 position on the alkyl group.

The crystalline zeolites utilizable in the process of this invention are characterized by the presence of channels or networks of pores through the crystal structure. These channels or networks of pores have openings thereto the major dimension of which is preferably between about six (6) and about seven (7) angstrom units. Specifically, the preferred zeolites include: cancrinite, gmelinite, mordenite, offretite, and synthetic and naturally-occurring isotypes thereof. A particularly preferred zeolite, the crystallographic structure of which is unknown at the present time, is the synthetic zeolite ZSM-12.

The process of this invention is carried out by contacting the phenolic compound with a suitable alkylating agent in the presence of the hereindisclosed novel type of shape selective zeolite catalyst, under conditions of temperature and pressure conducive to the desired alkylation reaction. Preferred conditions include temperatures of between about 50° C. and 500° C. and pressures of subatmospheric to about 100 atmospheres.

DESCRIPTION OF THE DRAWING

The single drawing FIGURE presents a series of superposed bar graphs illustrating a product spectrum obtained from the alkylation reaction of phenol with 1-octanol in the presence of four different alkylation catalysts, two of which fall within the scope of this invention. The FIGURE has been derived from Examples 1 thru 4.

DESCRIPTION OF SPECIFIC EMBODIMENTS

The invention contemplates the reaction of phenolic compounds with alkylating agents having an available, relatively long-chain alkyl group. The preferred phenolic compound is phenol, but other aromatic alcohols may be utilized to yield alkylation products having a beneficial product spectrum. Non-limiting examples of suitable aromatic alcohols would include: methylphenols (cresols); dimethylphenols (xylenols); ethyl, propyl and butylphenols; halophenols (e.g. chloro and bromo); alkylhalophenols; alkoxyphenols; dihydroxybenzenes (e.g. catechol, resorcinol); and so forth.

The alklylating agents useful in the process of this invention include any aliphatic or aromatic organic compound having one or more available alkyl groups capable of reacting with the phenolic compound. The alkyl group itself should have at least 5 carbon atoms, although groups having between 6 and 20 carbon atoms in the primary chain are generally preferred. Similarly, other aromatic compounds having available alkyl groups may be utilized, in which case the entire alkyl group may be transalkylated from the alkylaromatic to the phenolic compound, thereby forming the alkyl-substituted phenol. An exemplary octyl substituted aromatic compound would be, for instance, phenyloctane. Other suitable alkylating agents would include, for instance: olefins as octene, decene, dodecene and the like; alcohols having between 6 and 20 carbon atoms in the primary chain, especially mixed linear octanols, decanols, and dodecanols; and alkyl halides such as octyl chloride, dodecyl chloride and higher homologs. Branched alkylating agents, especially branched olefins such as propylene trimer or tetramer, are also utilizable.

The shape selective, crystalline zeolites utilized herein may be either naturally occuring or synthetic and include, by way of example, cancrinite, gmelinite, mordenite, dealuminized mordenite, offretite and ZSM-12. Also contemplated as being included herein are synthetic and naturally occurring isotypes of such zeolite materials, such as: zeolite S, zeolite Na-S, zeolite Na-D, Ptilolite, Zeolon, zeolite O, TMA-offetite, and others.

The crystal structure of the class of zeolites suitable for use as catalysts in the process of this invention is such as to provide access to and egress from the intracrystalline free space of the zeolites by virtue of having channels or networks of pores (hereinafter referred to as pores), the openings thereto preferably having a major dimension of between about 6 A and about 7 A. The zeolites utilized herein are further characterized as having pore apertures of about a size as would be provided by 12-member rings of silicon or aluminum atoms. It will be understood, of course, that these rings are those formed by the regular disposition of the tetrahedra making up the anionic framework of the crystalline zeolite, the silicon or aluminum atoms forming the centers of the tetrahedra and being themselves bonded together by oxygen atoms.

The pores characterizing the zeolites useful in the present process may be substantially circular, such as is the situation with respect to cancrinite which has uniform pores of about 6.2 angstroms, or may be somewhat elliptical, such as in the case of mordenite which has pores of approximately 6.7 by 7.0 angstroms. It should be understood that, in any case, the zeolites used as catalysts in the process of this invention have a major pore dimension intermediate between that of the large pore zeolites, such as the X and Y zeolites, and the relatively small pore size zeolites ZSM-5 and ZSM-11, and preferably between about 6 A and about 7 A. With the exception of zeolite ZSM-12, the pore size dimensions and crystal structures of the above zeolites are those specified in ATLAS OF ZEOLITE STRUCTURE TYPES by W. M. Meier and D. H. Olson, published by the Structure Commission of the International Zeolite Association (1978) and distributed by Polycrystal Book Service, Pittsburgh, Pennsylvania.

ZSM-12, the structure and pore size of which is unknown at the present time, is described in U.S. Pat. No. 3,832,449. That description, and in particular the characteristic crystal X-ray diffraction pattern disclosed therein, is incorporated herein by reference.

The zeolites useful in the conversion process of this invention generally have at least 10 percent of the cationic sites thereof occupied by ions other than alkali or alkaline-earth metals. Typical but non-limiting replacing ions include ammonium, hydrogen, rare earth, zinc, copper and aluminum. Of this group, particular preference is accorded ammonium, hydrogen, rare earth or combinations thereof. In a preferred embodiment, the zeolites are converted to the predominantly hydrogen form, generally by replacement of the alkali metal or other ion originally present with hydrogen ion precursors, e.g. ammonium ions. which upon calcination yield the hydrogen form. This exchange is conveniently carried out by contact of the zeolite with an ammonium salt solution, e.g. ammonium chloride, utilizing well known ion exchange techniques. The extent of replacement is such as to produce a zeolite material in which at least 50 percent of the cationic sites are occupied by hydrogen ions.

The zeolites may be subjected to various chemical treatments, including alumina extraction and combination with one or more metal components, particularly the metals of Groups IIB, III, IV, VI, VII and VIII of the Periodic Table. It is also contemplated that the zeolites may, in some instances, desirably be subjected to thermal treatment, including steaming or calcination in air, hydrogen or an inert gas such as nitrogen or helium.

An especially useful modifying treatment entails steaming of the zeolite by contact with an atmosphere containing from about 5 to about 100 percent steam at a temperature of from about 250° to 1000° C. Steaming may last for a period of between about 0.25 and about 100 hours and may be conducted at pressures ranging from subatmospheric to several hundred atmospheres to reduce the alpha value of the zeolite to less than 500, and preferably less than 20, but greater than zero.

In practicing the disclosed conversion process, it may be desirable in some instances to incorporate the above-described intermediate pore size crystalline zeolites in another material resistant to the temperature and other conditions employed in the process. Such matrix materials or "binders" include synthetic or naturally occuring substances as well as inorganic materials such as clay, silica, and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the intermediate pore size zeolites employed herein may be compounded with a porous matrix material, such as alumina, silica-alumina, silica-magnesia, silica-zirconia, silica-thoria, silica-beryllia, and silica-titania, as well as ternary combinations, such as silica-alumina-thoria, silica-alumina-zirconia, silica-alumina-magnesia and silica-magnesia-zirconia. The matrix may be in the form of a cogel. The relative proportions of finely divided zeolite and inorganic oxide gel matrix may vary widely with the zeolite content ranging from between about 1 to about 99 percent by weight and more usually in the range of about 5 to about 80 percent by weight of the composite.

The process of this invention is conducted such that the organic reactants, i.e. the phenolic compound and the alkylating agent, are brought into contact with the zeolite in a suitable reaction zone, such as for example a fixed bed of the catalyst, under effective alkylation conditions. Such conditions include a temperature of between about 50° C. and about 500° C., a pressure of between about $10^4$ N/m$^2$ (0.1 atmospheres) and about $10^7$ N/m$^2$ (100 atmospheres), and a feed weight hourly space velocity (WHSV) of between about 0.1 and about 200. The latter WHSV is based upon the weight of the catalyst compositions employed, i.e. the total weight of active catalyst and binder therefor. Preferred reaction conditions include a temperature within the approximate range of 100° C. to 400° C., with a feed WHSV of between 1 and 50. Although the reaction normally takes place at atmospheric pressure ($10^5$ N/m$^2$), the preferred pressure range extends from about $5 \times 10^4$ N/m$^2$ to about $5 \times 10^6$ N/m$^2$. The reactants may be in either the vapor phase or the liquid phase and may be neat, i.e. free from intentional admixture or dilution with other material, or may be brought into contact with the zeolite with the aid of carrier gases or diluents such as, for example, hydrogen, nitrogen, hydrocarbons, etc.

The alkylation process described herein may be carried out as a batch-type, semi-continuous or continuous operation utilizing a fixed or moving bed catalyst system. A preferred embodiment entails use of a catalyst zone wherein the hydrocarbon charge is passed concurrently or countercurrently through a moving bed of particle-form catalyst. The latter, after use, is conducted to a regeneration zone where coke is burned from the catalyst in an oxygen-containing atmosphere (such as air) at elevated temperature, after which the regenerated catalyst is recycled to the conversion zone for further contact with the organic reactants.

By practice of the hereindisclosed invention, one is able to advantageously react phenolic compounds with relatively long chain alkylating groups to yeild heretofore difficult to obtain alkylphenols which have several unexpected benefits. For one, attachment of the phenolic compound at the 2-position on the alkyl group is increased at the expense of the 3-, 4- and higher attachment. For another, para substitution of the phenolic compound is enhanced relative to ortho and meta substitution. Still another unexpected benefit to be realized, particularly when the shape selective catalyst employed is the zeolite ZSM-12, is that mono-alkylation of the phenolic compound is favored over di-alkylation. These and other advantages of the present invention will be evident from consideration of the following examples, which will serve to generally illustrate the disclosed novel process.

Example 1 (ZSM-12)

Phenol was alkylated with 1-octanol in the presence of zeolite HZSM-12 (silica/alumina ratio=90). The reaction was carried out in a flow reactor at 200°–250° C. and pressures of between 200 and 230 psig. The reactants, at a phenol/octanol mole ratio of 2:1, were passed over the catalyst at a feed WHSV, temperature and pressure as indicated in Table I. The reactor effluent was sampled and analyzed by gas-liquid chromatography (GLC). Product analysis is summarized in Table I. Percentages set forth in the Table represent relative GLC peak areas.

TABLE I

Alkylation of Phenol with 1-Octanol
Catalyst: ZSM-12

| Run No.: | 1 | 2 | 3 | 4 |
|---|---|---|---|---|
| Temperature | 200° C. | 250° C. | 250° C. | 250° C. |
| Pressure, psig | 220 | 200 | 230 | 230 |
| WHSV, hr$^{-1}$ | 30 | 30 | 10 | 10 |
| Time on stream, hr. | 0.9 | 2.8 | 2.0 | 29.5 |
| Products (Area %): | | | | |
| Octene | 0.8 | 9.4 | 0.9 | 1.0 |
| Phenol | 63.5 | 57.6 | 43.2 | 42.1 |
| Octanol | 34.3 | 3.9 | — | — |
| Octylphenol | 1.2 | 27.6 | 53.9 | 55.2 |
| Dioctylphenol | 0.2 | <0.1 | 0.4 | 0.1 |
| Other | <0.1 | 1.5 | 1.6 | 1.6 |
| Ratio of Mono- to Di-octylphenol | 7 | 394 | 135 | 460 |
| C$_8$ conversion | 17% | 72% | 98% | 98% |
| Selectivity to octylphenols* | 15% | 59% | 85% | 87% |
| Octylphenol Compositions | | | | |
| R—ϕ—OH | | | | |
| R = ortho-(2-octyl) | | | 16% | 21% |
| para-(2-octyl) | | | 37% | 34% |
| ortho-(3-octyl) | | | — | — |
| para-(3-octyl) | | | 41% | 36% |
| ortho-(4-octyl) | | | — | — |
| para-(4-octyl) | | | — | — |
| other octyl | | | 6% | 9% |

Notes:
*Based on C$_8$ reacted.

Example 2 (Mordenite, dealuminized)

A sample of mordenite (Norton Zeolon Type 100 H, silica/alumina mole ratio=10) was air calcined for one hour at 600° C. The material was refluxed for 20 hours with 0.5 N HCl (50 ml of solution per gram of zeolite) and then refluxed for 20 hours with distilled water. After removal of the water and drying, the silica to alumina ratio of the resulting dealuminized mordenite was determined to be 93.

In a series of runs, phenol and 1-octanol (mole ratio 2:1) were passed over a sample of the above material at 225° C. and 200 psig, with the feed rate (WHSV) varying between 5 hr$^{-1}$ and 30 hr$^{-1}$. Table II is a summary of the run conditions and products.

TABLE II

Alkylation of Phenol with 1-Octanol
Catalyst: Dealuminized Mordenite

| Run No.: | 1 | 2 | 3 |
|---|---|---|---|
| Temperature | 225° C. | 225° C. | 225° C. |
| Pressure, psig | 200 | 200 | 200 |
| WHSV, hr$^{-1}$ | 5 | 10 | 30 |
| Time on stream, hr. | 7-22 | 25 | 0.8 |
| Products (Area %) | | | |
| Octene | <0.1 | 0.6 | 0.3 |
| Phenol | 45.8 | 46.7 | 57.9 |
| Octanol | 5.0 | 5.8 | 16.8 |
| Octylether | 7.1 | 9.2 | 6.4 |
| Octylphenol | 33.8 | 29.8 | 14.4 |
| Octylphenylether | 2.6 | 3.0 | 1.5 |
| Dioctylphenol | 5.8 | 4.8 | 0.8 |
| Other | — | 0.1 | 1.8 |
| Ratio of Mono- to Di-octylphenol | 6 | 6 | 17 |
| C$_8$ conversion** | 73% | 64% | 46% |
| Selectivity to octylphenols* | 99% | ~100% | 61% |
| Octylphenol composition | | | |
| R—ϕ—OH | | | |
| R = para-(1-octyl) | + | 4.4% | 2.6% |
| ortho-(2-octyl) | 31.3% | 25.2% | 24.9% |
| para-(2-octyl) | 48.0% | 48.7% | 48.7% |
| ortho-(3-octyl) | + | + | — |
| para-(3-octyl) | 20.7% | 19.3% | 21.5% |
| ortho-(4-octyl) | — | — | — |
| para-(4-octyl) | — | — | — |
| other octyl | + | 2.2% | 2.4% |

Notes:
*Based on C$_8$ reacted; includes octylphenylether.
+Trace detected.
**Octene, octanol, and octylether are considered unreacted C$_8$.

Example 3 (REY)

Using substantially the same reaction conditions as in Examples 1 and 2, phenol was alkylated with 1-octanol (mole ratio 2:1) over a conventional zeolite alkylation catalyst (REY) having a pore opening of 7.4 A. Run conditions and product analysis are summarized in Table III.

TABLE III

Alkylation of Phenol with 1-Octanol
Catalyst: Zeolite REY

| Run No.: | 1 | 2 | 3 |
|---|---|---|---|
| Temperature | 250° C. | 250° C. | 200° C. |
| Pressure, psig | 200 | 200 | 200 |
| WHSV, hr$^{-1}$ | 10 | 30 | 30 |
| Time on stream, hr. | 3.3 | 1.7 | 1.0 |
| Products (Area %): | | | |
| Octene | — | 0.3 | 0.1 |
| Phenol | 56.5 | 53.8 | 59.0 |
| Octanol | 22.3 | 18.9 | 30.2 |
| Octylphenol | 19.6 | 24.5 | 10.1 |
| Dioctylphenol | 0.1 | — | — |
| Other | 0.6 | 0.2 | 0.6 |
| Ratio of Mono- to Di-octylphenol | | | |
| C$_8$ conversion | 50% | 57% | 29% |
| Selectivity to octylphenols* | 66% | 77% | 61% |
| Octylphenol composition | | | |
| R—ϕ—OH | | | |
| R = ortho-(2-octyl) | | 12% | |
| para-(2-octyl) | | 20% | |
| ortho-(3-octyl) | | 12% | |
| para-(3-octyl) | | 25% | |
| ortho-(4-octyl) | | 13% | |
| para-(4-octyl) | | 17% | |

TABLE III-continued

| Alkylation of Phenol with 1-Octanol | | | |
|---|---|---|---|
| Catalyst: Zeolite REY | | | |
| Run No.: | 1 | 2 | 3 |
| other octyl | | 2% | |

Notes:
*Based on $C_8$ reacted.

Example 4 (Amberlyst-15)

A mixture of phenol and 1-octene (mole ratio=10:1) was placed in a flask equipped with a reflux condenser together with a strongly acidic ion exchange resin (Amberlyst-15) in an amount equal to about 10 wt.% of the mixture. The flask was heated to 125° C. and held at that temperature for one hour. At the end of the hour, the organic liquid was separated from the solid resin and analyzed by GLC.

In a second run, the phenol to 1-octene mole ratio was changed to 2:1 and the reaction repeated as above. The results of both runs are summarized in Table IV.

TABLE IV

| Alkylation of Phenol With 1-Octene | | |
|---|---|---|
| Catalyst: Amberlyst-15 | | |
| Run No.: | 1 | 2 |
| Mole ratio of reactants | 10:1 | 2:1 |
| Temperature | 125° C. | 125° C. |
| Pressure, psig | ambient | ambient |
| Reaction Time, hr | 1 | 1 |
| Products (Area %) | | |
| Octene | — | 0.9 |
| Phenol | 85.4 | 35.5 |
| Octylphenol | 14.7 | 61.1 |
| Dioctylphenol | 0 | 2.5 |
| Ratio of Mono- to Di-octylphenol | >100 | 25 |
| $C_8$ conversion | 100% | 98% |
| Selectivity to octylphenols* | 88% | 100% |
| Octylphenol composition | | |
| R—φ—OH | | |
| R = ortho-(2-octyl) | 28% | |
| para-(2-octyl) | 15% | |
| ortho-(3-octyl) | 15% | |
| para-(3-octyl) | 20% | |
| ortho-(4-octyl) | 10% | |
| para-(4-octyl) | 11% | |
| other octyl | 0% | |

Notes:
*Based on $C_8$ = reacted.

Comparing Examples 1 thru 4, it will be seen that the octylphenol product spectrum resulting from use of catalysts encompassed within the foregoing novel description (i.e.: ZSM-12 and Mordenite) is very different from that resulting from the reactions involving the more conventional alkylation catalysts (REY and Amberlyst-15). The FIGURE, which is a series of superposed bar graphs representing the octylphenol compositions resulting from the illustrated catalyst systems and derived from the data of Examples 1 thru 4, clearly shows the unique character of the octylphenol mixture resulting from the process of this invention.

REY and Amberlyst-15 gave similar product spectrums, both consisting of complicated mixtures with no particular or outstanding preference to any aromatic ring substitution position nor to any particular point of attachment of the phenol on the alkyl chain. In sharp contrast, the octylphenols produced as a result of utilization of the novel class of zeolites encompassed within the scope of the present invention, as represented by ZSM-12 and Mordenite, were unexpectedly rich in both para-octylphenols and in octylphenols in which the aromatic ring was attached at the 2-position on the alkyl chain.

Another unique benefit to be realized from the process of this invention will be seen in the surprising specificity of the reaction to mono-alkylphenols as compared to the disubstituted product. This is particularly evident in the reaction involving ZSM-12 (Example 1), where the ratio of mono-alkylphenol to di-alkylphenol is shown to be as high as 460/1.

The unique and substantial benefits of the disclosed invention are not limited to production of $C_8$ phenols, as will be seen from the following:

Example 5

Using a sample of the dealuminized Mordenite from Example 2, phenol was reacted with 1-dodecanol to produce dodecylphenol. The feed stream, consisting of phenol and 1-dodecanol at a mole ratio of 2:1, was passed over the catalyst at 250° C., 300 psig and WHSV of 10 hr$^{-1}$. The results are summarized in Table V. A run using Amberlyst-15 to react phenol and dodecene-1 in the same manner as outlined with respect to Example 4 is presented for purposes of comparison.

TABLE V

| Alkylation of Phenol with $C_{12}$ | | |
|---|---|---|
| Catalyst: | Mordenite | Amberlyst-15 |
| Temperature | 250° C. | 125° C. |
| Pressure, psig | 300 | ambient |
| WHSV | 10 | — |
| Products (Area %) | | |
| Phenol | 40.1 | |
| Dodecene | 3.5 | |
| Dodecanol | 2.2 | |
| Dodecylphenol | 51.3 | |
| Dodecylether | 0.6 | |
| Other | 2.3 | |
| $C_{12}$ conversion | 88% | |
| Selectivity to dodecylphenols* | 71% | |
| Dodecylphenol composition | | |
| para-(2-$C_{12}$)φ—OH | 41.0% | 11.1% |
| para-(3-$C_{12}$)φ—OH | 15.8% | 8.0% |
| para-(4-$C_{12}$)φ—OH | 1.1% | 4.4% |
| para-(5-$C_{12}$)φ—OH / para-(6-$C_{12}$)φ—OH / ortho-(2-$C_{12}$)φ—OH | 29.8% | 34.6% |
| ortho-(3-$C_{12}$)φ—OH | 5.1% | 16.4% |
| ortho-(4-$C_{12}$)φ—OH | 0% | 9.3% |
| ortho-(5-$C_{12}$)φ—OH | 0% | 8.2% |
| ortho-(6-$C_{12}$)φ—OH | 0% | 8.1% |
| other $C_{12}$φ—OH | 7.2% | — |

Notes:
*Based on $C_{12}$ reacted.

Compared with the dodecylphenol product mix formed from the reaction of dodecene-1 and phenol over Amberlyst-15 ion exchange resin, it is seen that, as in the example to alkylation with $C_8$, mordenite again has given enhanced yield of both para and 2-dodecylphenols.

It is to be understood that the foregoing specific examples are intended to be merely illustrative of the process of the present invention. Many variations and modifications thereof may be made without departing from the spirit of the disclosure, as will readily apparent to those skilled in the pertinent chemical arts. Such variations and modifications are intended to be encompassed within the scope and purview of the following claims.

What is claimed is:

1. A process for the production of alkyl-substituted phenolic compounds comprising:

contacting a phenol with an alkylating agent having a reactive alkyl group at a temperature of between about 50° C. and about 500° C. and a pressure within the approximate range of $10^4$ N/m$^2$ to $10^7$ N/m$^2$, said alkyl group having at least 5 carbon atoms, said contacting being in the presence of a crystalline zeolite catalyst which is characterized by the presence therein of networks of pores having openings thereto, the major dimension of said openings being between about six and about seven angstroms.

2. A process as defined in claim 1 wherein said temperature is between about 100° C. and about 400° C.

3. A process as defined in claim 2 wherein said pressure is between about $5 \times 10^4$ N/m$^2$ and about $5 \times 10^6$ N/m$^2$.

4. A process as defined in claim 1 wherein said alkyl group contains from about 6 to about 20 carbon atoms in the primary carbon chain.

5. A process as defined in claim 1 wherein said alkyl-substituted phenolic compound produced thereby contain a substantial amount of the isomer wherein the phenolic moiety is attached to the 2-position on the alkyl moiety.

6. A process as defined in claim 1 wherein said alkyl-substituted phenolic compound produced thereby are enriched with respect to the para-alkylphenolic isomer thereof.

7. A process as defined in claim 1 wherein said crystalline zeolite additionally comprises a binder therefor.

8. A process as defined in claims 1, 2, 3, 4, 5, 6 or 7 wherein said crystalline zeolite is chosen from the group consisting of: cancrinite, gmelinite, mordenite, offretite, ZSM-12 and synthetic or naturally-occurring isotypes thereof.

9. A process as defined in claims 1, 2, 3, 4, 5, 6 or 7 wherein said zeolite has the crystal structure of cancrinite.

10. A process as defined in claims 1, 2, 3, 4, 5, 6 or 7 wherein said zeolite has the crystal structure of gmelinite.

11. A process as defined in claims 1, 2, 3, 4, 5, 6 or 7 wherein said zeolite has the crystal structure of mordenite.

12. A process as defined in claims 1, 2, 3, 4, 5, 6 or 7 wherein zeolite has the crystal structure of offretite.

13. A process as defined in claims 1, 2, 3, 4, 5, 6 or 7 wherein said zeolite has the crystal structure of ZSM-12.

14. A process as defined in claim 1 wherein said crystalline zeolite has been subjected to treatment to remove at least some of the aluminum atoms therein prior to use.

15. A process as defined in claim 1 wherein said zeolite has been steamed prior to use.

* * * * *